(12) United States Patent
Aramata et al.

(10) Patent No.: US 6,686,312 B1
(45) Date of Patent: *Feb. 3, 2004

(54) METALLIC COPPER CATALYST AND PROCESS FOR MAKING ORGANOHALOSILANES

(75) Inventors: Mikio Aramata, Annaka (JP); Masaaki Furuya, Annaka (JP); Yoshihiro Shirota, Annaka (JP); Akio Muraida, Annaka (JP); Susumu Ueno, Annaka (JP); Toshio Shinohara, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/522,690

(22) Filed: Mar. 10, 2000

(30) Foreign Application Priority Data

Mar. 11, 1999 (JP) .......................................... 11-064335

(51) Int. Cl.⁷ .............................................. B01J 23/70
(52) U.S. Cl. ...................... 502/345; 502/343; 556/472
(58) Field of Search ................................ 502/345, 343; 556/472

(56) References Cited

U.S. PATENT DOCUMENTS 5,817,855 A   10/1998   Langner et al. ............. 556/472
6,365,766 B1 *  4/2002   Aramata et al. ............ 556/472

FOREIGN PATENT DOCUMENTS

JP     9-173844     7/1997
JP    10-309465    11/1998

OTHER PUBLICATIONS

Patent Abstracts of Japan, Publication No. 10309465 date Nov. 24, 1998.

* cited by examiner

Primary Examiner—Porfirio Nazario-Gonzalez
(74) Attorney, Agent, or Firm—Millen, White, Zelano & Branigan, P.C.

(57) ABSTRACT

In the synthesis of organohalosilanes by the direct process of reacting an organic halogen with metallic silicon powder, a metallic copper catalyst in the form of a thermally active metallic copper powder having large strain energy is used.

8 Claims, 2 Drawing Sheets

METALLIC COPPER CATALYST AND PROCESS FOR MAKING ORGANOHALOSILANES

This invention relates to a process for preparing organohalosilanes by the so-called Rochow reaction and a copper catalyst used therein.

BACKGROUND OF THE INVENTION

The Rochow reaction is typically employed in the industrial process for the synthesis of organohalosilanes such as methylchlorosilanes. The Rochow reaction is the direct reaction of organic halides such as alkyl halides and phenyl halides with metallic silicon particles which is carried out at 250 to 500° C. in the presence of a copper catalyst. While this reaction requires to keep a high reaction rate, a key technology in the synthesis of methylchlorosilanes is to increase the selectivity of the most desirable dimethyldichlorosilane. A key technology in the synthesis of phenylsilanes is to produce the most desirable diphenyldichlorosilane and phenyltrichlorosilane in a composition matching with their demand.

More particularly, organohalosilanes are synthesized by the Rochow reaction which is gas-phase direct reaction involving passing an organic halide gas such as methyl chloride through a contact mass consisting of metallic silicon, a copper catalyst and a minor amount of a co-catalyst. Since the cost of metallic silicon accounts for a substantial proportion of the raw material cost, it is important for this reaction to take place at an increased reaction rate of metallic silicon. Since a variety of by-products usually form in this reaction in addition to the main product diorganodichlorosilane, it is also important to control the reaction conditions to form the by-products in such a proportion as to comply with the supply/demand balance of organochlorosilanes. Industrially, the reaction is generally carried out in a reactor such as a fluidized bed, vibrating fluidized bed or agitating fluidized bed while replenishing the contact mass to the reaction system. It is quite important to effect reaction while reducing the activation time (that is the time taken for activation until the reaction reaches a steady state), preventing a lowering of activity with the progress of reaction due to deposition of deactivated contact mass, that is, preventing a decline of reaction rate and selectivity, and minimizing the increase of reactor residues (high boiling fractions such as disilanes) which are essentially unnecessary components.

However, the conventional Rochow reaction requires a very long time for activation until the reaction reaches a steady state. The steady state, in turn, is relatively short. The contact mass's activity lowers with the lapse of time, and the yield of diorganodichlorosilane decreases accordingly. In the synthesis of methylchlorosilanes, for example, there arise problems that high-boiling fractions such as disilanes and undesired products such as methyltrichlorosilane increase due to side reaction. This necessitates to exchange the contact mass in the reactor. In order to shorten the initial activation time among the above-described many factors, it is known effective to add a copper catalyst after only metallic silicon powder is preheated to nearly the reaction temperature, thereby preventing the sintering of the copper catalyst by thermal history (see JP-A 10-309465).

When reaction is carried out by this procedure, unfortunately, the results of reaction vary over a wide range. It is desired to solve the problem of process variances.

SUMMARY OF THE INVENTION

The inventor investigated why the results of reaction vary over a wide range even when reaction is carried out under identical conditions. It has been found that the activity of the copper catalyst used in the relevant reaction is largely dependent on the magnitude of strain energy of the crystal lattice that the copper catalyst possesses (simply referred to as strain energy, hereinafter) and that a large quantity of strain energy and a large surface area are essential requirements for the copper catalyst to exert a high activity. More particularly, in this reaction, the copper catalyst is mixed with metallic silicon powder and acts on an alkyl halide (e.g., methyl chloride) or aryl halide (e.g., phenyl chloride) to help produce a corresponding organochlorosilane. The reactivity largely depends on the activity of the copper catalyst. Since this reaction is basically a gas-solid heterogeneous reaction between the organic halide which becomes gaseous at high temperatures and the copper catalyst which remains solid even at high temperatures, it is fully expectable that the surface activity of the copper catalyst is crucial. Nevertheless, not only such action of the copper catalyst itself, but also the necessary characteristics of the copper catalyst are unknown. When copper oxide is used as the catalyst in this reaction, it is already known from JP-A 9-173844, U.S. Pat. Nos. 4,520,130 and 4,504,597 that the strain energy in the copper oxide powder is crucial to the activity thereof. In these patents, the concept of strain energy is merely described, the illustrative method of measuring strain energy is not described, and no reference is made to metallic copper catalysts. With the metallic copper catalyst, the process of these patents cannot be industrially carried out.

The inventor has found that the above-mentioned problems can be solved by using a metallic copper powder having a large quantity of strain.energy and hence, a highly active surface as the metallic copper catalyst for the Rochow reaction of synthesizing organohalosilanes which is capable of maintaining a high activity in a stable manner. In particular, use is made of a metallic copper catalyst in which the strain energy of crystal lattices it possesses is relaxed at a temperature below 300° C. and which has a specific surface area of 0.05 to 2 $m^2/g$ as measured by the BET method or air-permeability method. Alternatively, use is made of a metallic copper catalyst in which when heated in air, the surface is rapidly oxidized in unison with the relaxation of the strain energy, the heat generation start temperature as measured by air-flow differential thermal analysis (DTA) is below 300° C., and the calorific value produced is 1 to 80 cal/g. The use of the above-defined metallic copper catalyst solves the problems of prior art Rochow reaction, increases the selectivity of desired diorganodihalosilane without a variation in reaction results, and eventually improves the reaction results. The present invention is predicated on this finding.

Accordingly, the invention in one aspect provides a metallic copper catalyst for use in the synthesis of organohalosilanes, comprising a thermally active metallic copper powder having a large quantity of strain energy. In another aspect, the invention provides a method for preparing an organohalosilane by reacting an organic halide with metallic silicon particles in the presence of the metallic copper catalyst defined above. In one preferred embodiment, a copper foil powder, stamped copper powder or microscopic copper powder is used as the metallic copper powder. The copper catalyst should preferably have a specific surface area of 0.05 to 2 $m^2/g$ as measured by the BET method or air-permeability method. The copper catalyst should preferably have a heat generation start temperature of up to 300° C. and produce a calorific value of 1 to 80 cal/g as measured by air-flow differential thermal analysis.

The metallic copper catalyst used herein is a metallic copper powder having a large quantity of strain energy, for example, ground powder or chopped powder of rolled metallic copper foil, stamped copper powder obtained by drawing and grinding rolled copper foil or machined copper plates as by stamping, or microscopic copper fines. When copper powder of this type is heated in air, the strain energy is relaxed all of a sudden at a temperature below 300° C., rapid oxidation of the surface occurs concomitantly, and substantial heat generation is observed. In connection with the Rochow reaction, that is, the organohalosilane synthesis reaction between an alkyl halide (e.g., methyl chloride) or aryl halide (e.g., benzene chloride) and metallic silicon in the presence of a copper catalyst and a co-catalyst, the present invention uses the above-defined catalyst to solve the problem of the prior art technology that the activation time (or induction period) taken until the reaction rate and selectivity of silane synthesis reach a steady state is very long while the steady state continues relatively short.

DESCRIPTION OF THE PREFERRED EMBODIMENTS

The organohalosilane preparing process of the invention relies on the silane direction reaction or Rochow reaction. That is, organohalosilanes are synthesized by contacting an organic halide such as an alkyl halide or aryl halide in gas or vapor form with metallic silicon powder in the presence of a metallic copper catalyst. According to the invention, a metallic copper powder having a large quantity of strain energy is used as the metallic copper catalyst, thereby reducing the activation time (or induction period) taken until the reaction reaches a steady state, which has been the neck of the Rochow reaction, and maintaining a high activity in the steady state.

The metallic copper powder having a large quantity of strain energy is available as copper foil powder obtained by comminuting rolled copper foil, stamped copper powder obtained by drawing and comminuting rolled copper foil, electrolytic copper foil or machined copper chips, or microscopic copper fines such as atomized copper. A thermally active metallic copper powder having a large quantity of strain energy in the interior is used. It is noted that the greater the strain energy in the copper powder, the lower becomes the temperature at which it is relaxed. A metallic copper catalyst having a relaxation temperature below 300° C. is preferred, and additionally its surface presenting active sites gives a specific surface area of 0.05 to 2 $m^2/g$ as measured by the BET method or air-permeability method. When heated in air, copper powder shows such a behavior that as the strain energy is relaxed, the surface is rapidly oxidized. Then when a copper catalyst is analyzed by differential thermal analysis (DTA) in an air stream, a high exothermic peak is observed. A metallic copper catalyst having a heat-generation starting temperature below 300° C. and a calorific value of 1 to 80 cal/g is preferably used.

Figure 1A:
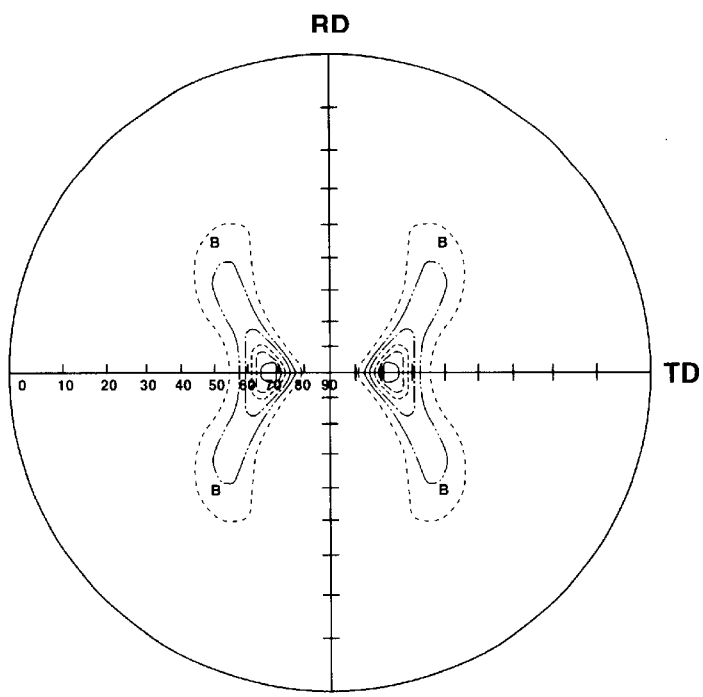
FIG. 1 is an x-ray diffraction diagram of rolled copper showing a pole pattern of [200] axis (in direction B) relative to (100) face, FIG. 1A corresponding to rolled copper and FIG. 1B corresponding to rolled copper as annealed at 300° C.
Figure 1B:
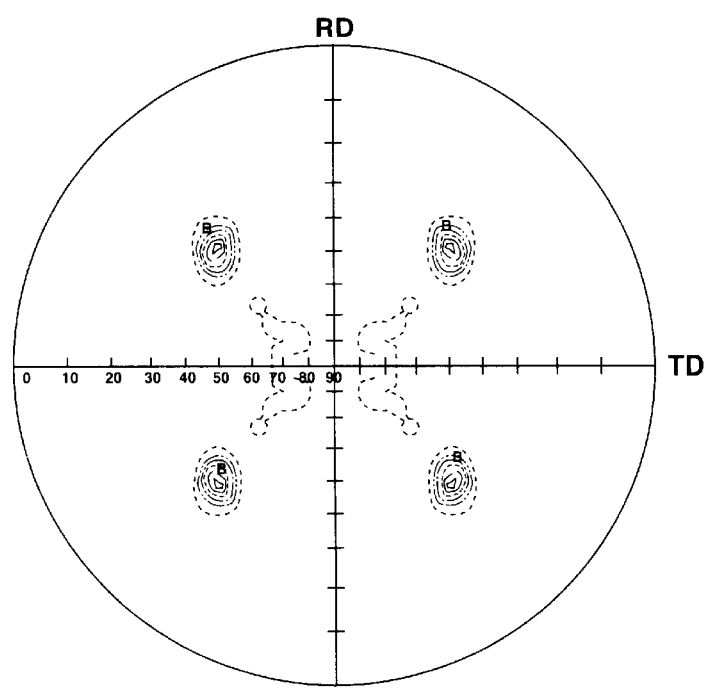

More illustratively, the key of the invention resides in the strain and energy involved in a metallic copper catalyst. Since metallic copper is highly ductile, it can be readily worked, as by rolling and forging, even at low temperature. Such working causes large lattice distortion to be generated in the crystals. That distortion is stored unless heated. Since heating the copper in an inert gas extinguishes the distortion and largely changes the physical properties, this heating is generally called annealing and is an important operation in the working process. The result of measurement of this crystallographic change is shown in FIG. 1. By referring to FIG. 1, the change is described in more detail. FIG. 1 is a pole diagram showing the data obtained by analyzing crystal faces and crystal axes using an x-ray diffraction instrument, from which the orientation of the crystal is determinable. The actual copper catalyst is in powder form and the measurement on such powder is difficult. Thus measurement was made on a rolled copper foil whose crystal lattice is largely distorted. As seen from the results of FIG. 1A, the surface of rolled copper foil consists of (111) face and [200] axes are strongly oriented from that face in one direction at an angle of about 70 degrees, which are significantly different from the stable theoretical values designated B in the diagram. By contrast, as seen from FIG. 1B showing the analytical data on the rolled copper foil as heated at 300° C. in an inert gas, [200] axes are oriented at an angle of about 35 degrees and are equidistantly spaced at an angle of about 90 degrees, which is a stable orientation conforming to the theoretical values, indicating a stable crystal structure. By heat treating a rolled copper foil at 300° C. in an inert gas, the foil is annealed so that the lattice distortion produced during rolling is relaxed.

Figure 2:
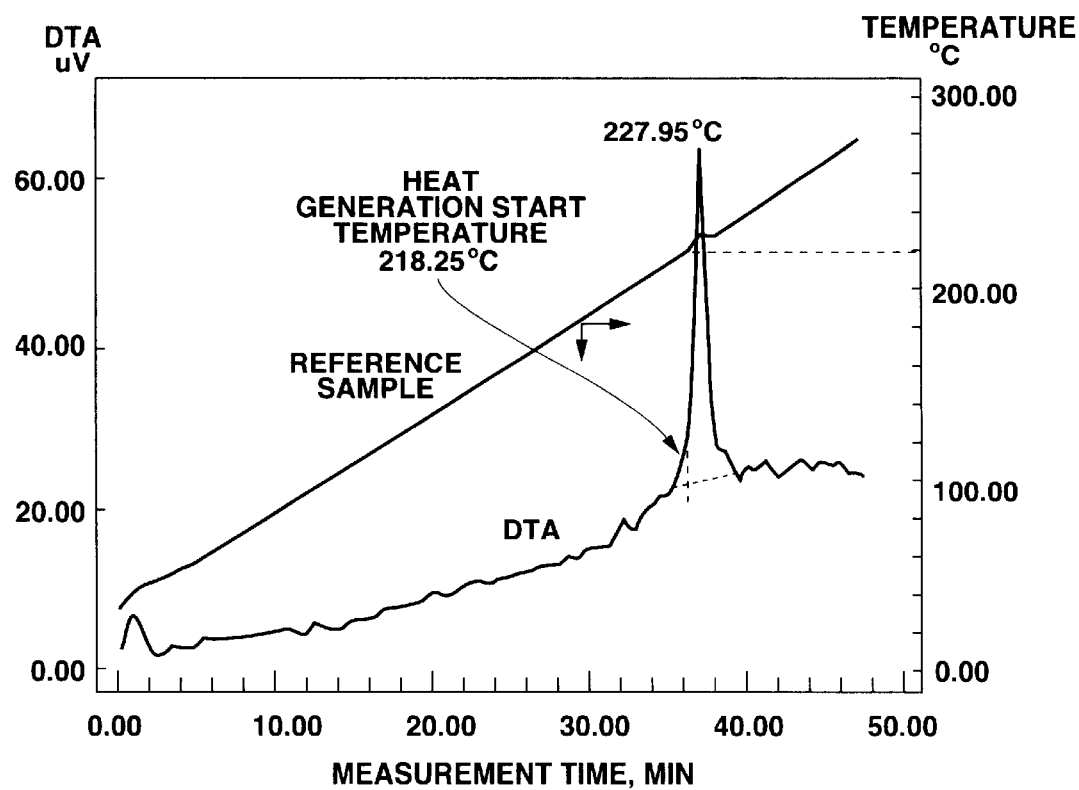
FIG. 2 is a diagram of a strained copper powder (stamped copper) as analyzed by a differential thermobalance.

FIG. 2 shows the results of differential thermobalance measurement on stamped copper powder in air. An abrupt heat generation occurs from about 220° C. and a concomitant rapid weight increase is observed. Thereafter, a gradual weight increase takes place, which indicates that oxidation slowly proceeds into the interior. Notably, such a change is not observed on the sample which is previously heated at 300° C. in an inert gas. Then the change indicates that atoms are rearranged in unison with the relaxation of strain energy and at this point, the surface becomes extremely active. Namely, the heat-generation starting temperature and the heat quantity (calorific value) represent just the surface activity of the metallic copper catalyst.

The activity of the copper catalyst for the Rochow reaction according to the invention is such that the copper catalyst possesses large crystal lattice distortion which is abruptly relaxed when the catalyst is introduced into the Rochow reaction system above the relaxation temperature. At this point, rearrangement of copper atoms occurs whereby an active copper surface develops abruptly. Then the activity of the copper catalyst can be determined in terms of the heat-generation starting temperature, at which oxidation starts, and the calorific value as analyzed by differential thermal analysis (DTA) or differential scanning calorimeter (DSC) in an air atmosphere or air stream, and the specific surface area, which is the surface area of the catalyst itself, as measured by the BET method or air-permeability method.

Of these analyses, the differential thermal analysis (DTA) is carried out by heating in a measuring atmosphere (in this case, air atmosphere) a test sample and a reference substance, which is thermally stable in the measuring atmosphere, at a constant rate (e.g., 5° C./min) and measuring the temperature difference between the test sample and the reference sample (in this case, α-alumina powder). Then a thermal change occurring in the test sample is detected as the temperature difference. Since distortion having a greater quantity of energy is relaxed at a lower temperature, a sample which starts heat generation at a lower temperature and has a larger surface area is measured as providing a higher exothermic peak. The BET specific surface area is measured by way of adsorption of a gas, and the air-permeability method specific surface area is measured in terms of the air resistance. These factors are correlated to the ease of contact with a gas.

For a variety of copper catalysts, these physical properties and reactivity were compared. It has been found that a copper powder having a heat generation start temperature of up to 300° C. and a calorific value of 1 to 80 cal/g, when subject to differential thermal analysis by heating at a rate of 5° C./min, and a specific surface area of 0.05 to 2 m$^2$/g is advantageous as the Rochow reaction catalyst.

Preferably, the heat generation start temperature is 100 to 300° C., more preferably 100 to 250° C., further preferably 150 to 250° C., and most preferably 150 to 230° C. The calorific value is preferably 1.0 to 80 cal/g, and more preferably 10 to 60 cal/g. The specific surface area is preferably 0.05 to 2.0 m$^2$/g, and more preferably 0.3 to 1.0 m$^2$/g.

An appropriate particle diameter of the copper catalyst may be selected over a wide range, although the preferred catalyst has a particle diameter of 0.05 to 100 μm, and more preferably 20 to 80 μm as measured by a laser diffraction particle size measuring instrument.

Excepting the use of the above-defined copper catalyst, the organohalosilane preparing process of the invention may be carried out by employing any well-known procedure and conditions. For example, the metallic silicon particles used as one reactant may have a mean particle size of about 10 μm to about 10 mm. The organic halide used as the other reactant may be selected from alkyl halides and aryl halides having an alkyl or aryl group corresponding to a desired organohalosilane, for example, methyl chloride, ethyl chloride, and phenyl chloride. According to the invention, organohalosilanes of the following formula:

$$R_n SiX_{4-n}$$

wherein R is $C_{1-4}$ alkyl or aryl such as phenyl, X is a halogen atom such as chlorine or bromine, and "n" is an integer of 1 to 4, especially diorganodihalosilanes wherein n=2, can be produced in high yields.

The amount of the copper catalyst added may be about 0.1 to about 10 parts by weight per 100 parts by weight of the metallic silicon. Any of well-known co-catalysts may be added to the copper catalyst.

Figure 3:
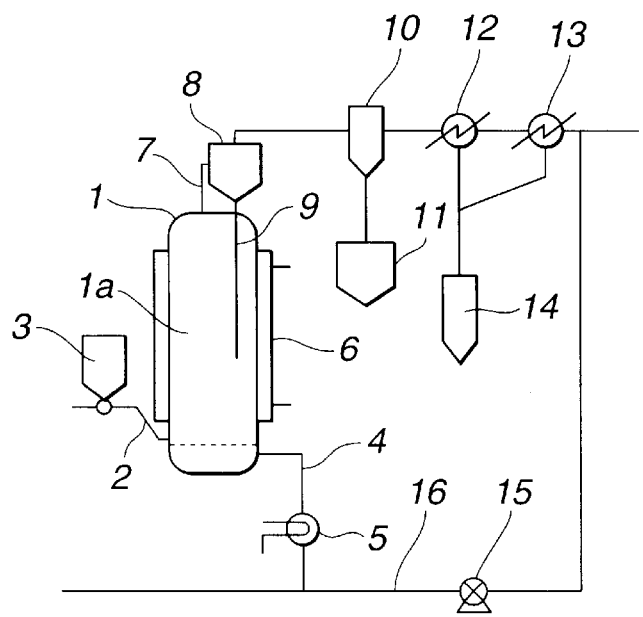
FIG. 3 schematically illustrates a system for the preparation of organohalosilanes.

FIG. 3 illustrates a system for preparing organohalosilanes. The system includes a fluidized bed reactor 1 and a reactant source tank 3 connected to the bottom of the reactor 1 through a reactant feed conduit 2, whereby metallic silicon and a copper catalyst or a mixture of a copper catalyst and a co-catalyst are admitted into the bottom of the reactor 1. A conduit 4 for the other reactant, organic halide has a heater 5 inserted therein and is connected to the reactor 1 at the bottom. The organic halide in gas or vapor form is also introduced into the bottom of the reactor 1, thereby forming a fluidized bed 1a of the metallic silicon and the catalyst within the reactor 1. The reactor 1 is enclosed with a cooling jacket 6.

Preferably the organic halide in gas or vapor form is introduced into the reactor 1 at a linear velocity of 2 to 10 cm/sec in the steady state. Reaction is generally carried out at a temperature of 250 to 350° C.

The organohalosilane product resulting from the reaction is channeled through a discharge conduit 7 connected to the top of the reactor 1 to a first cyclone 8 where the entrained solid particles are separated and fed back to the fluidized bed 1a through a return pipe 9. The product is then fed to a second cyclone 10 where the entrained solid particles are separated and fed to a particle reservoir 11 for storage. The product is then fed to first and second silane condensers 12 and 13 where the organohalosilanes are condensed and fed to a silane reservoir 14 for storage. Part or all of the discharge gas from which solid particles have been separated and organohalosilanes have been condensed and separated is fed back to the reactor 1 through an organic halide return conduit 16 having a recycle gas compressor 15 inserted therein. The return conduit 16 is connected to the organic halide feed conduit 4.

EXAMPLE

Examples of the invention are given below by way of illustration and not by way of limitation. All parts are by weight.

Example 1

Using a system as shown in FIG. 3, methylchlorosilanes were prepared. A steel reactor of 8 cm in diameter equipped with a spiral agitator was charged with 100 parts of metallic silicon powder having a mean particle size of 50 μm. With stirring, nitrogen gas was introduced into the reactor at a linear velocity of 2 cm/sec to fluidize the silicon powder while the powder was heated to 280° C. Thereafter, 3 parts of a catalyst mixture was added to the reactor. The catalyst mixture consisted of a stamped copper catalyst having an air-permeability method specific surface area of 0.88 m$^2$/g, a DTA heat generation start temperature of 218° C., and a calorific value of 24.9 cal/g at the exothermic peak and a co-catalyst composed mainly of brass and bronze. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. After 6 hours, the reaction was stopped. The average rate of silane production, percent consumption of metallic silicon, and the composition of the formed silanes are shown in Table 1.

Example 2

As in Example 1, the reactor charged with 100 parts of metallic silicon powder having a mean particle size of 50 μm was heated to 280° C. in a nitrogen gas stream. Thereafter, 3 parts of a catalyst mixture was added to the reactor. The catalyst mixture consisted of a stamped copper catalyst having an air-permeability method specific surface area of 0.30 m$^2$/g, a DTA heat generation start temperature of 230° C., and a calorific value of 7.6 cal/g at the exothermic peak and a co-catalyst composed mainly of brass and bronze. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. After 6 hours, the reaction was stopped. The average rate of silane production, percent consumption of metallic silicon, and the composition of the formed silanes are shown in Table 1.

Example 3

As in Example 1, the reactor charged with 100 parts of metallic silicon powder having a mean particle size of 50 μm was heated to 280° C. in a nitrogen gas stream. Thereafter, 3 parts of a catalyst mixture was added to the reactor. The catalyst mixture consisted of a stamped copper catalyst having an air-permeability method specific surface area of 1.4 m²/g, a DTA heat generation start temperature of 159° C., and a calorific value of 52.7 cal/g at the exothermic peak and a co-catalyst composed mainly of brass and bronze. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. After 6 hours, the reaction was stopped. The average rate of silane production, percent consumption of metallic silicon, and the composition of the formed silanes are shown in Table 1.

Example 4

As in Example 1, the reactor charged with 100 parts of metallic silicon powder having a mean particle size of 50 µm was heated to 280° C. in a nitrogen gas stream. Thereafter, 3 parts of a catalyst mixture was added to the reactor. The catalyst mixture consisted of a stamped copper catalyst having an air-permeability method specific surface area of 0.30 m²/g, a DTA heat generation start temperature of 230° C., and a calorific value of 7.6 cal/g at the exothermic peak and a co-catalyst in the form of an alloy powder composed mainly of brass and bronze with antimony added thereto. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. After 6 hours, the reaction was stopped. The average rate of silane production, percent consumption of metallic silicon, and the composition of the formed silanes are shown in Table 1.

Comparative Examples 1 and 2

As in Example 1, the reactor charged with 100 parts of metallic silicon powder having a mean particle size of 50 µm was heated to 280° C. in a nitrogen gas stream. Thereafter, 3 parts of a catalyst mixture consisting of a copper catalyst and a co-catalyst composed mainly of brass and bronze was added to the reactor. The copper catalyst used was obtained by starting with a stamped copper catalyst having an air-permeability method specific surface area of 0.88 m²/g, a DTA heat generation start temperature of 218° C., and a calorific value of 24.9 cal/g at the exothermic peak and annealing it at 300° C. in nitrogen gas whereby the DTA exothermic peak disappeared and the air-permeability method specific surface area was changed to 0.70 m²/g. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. After 6 hours, the reaction was stopped (Comparative Example 1).

In another run (Comparative Example 2), an electrolytic copper powder having an air-permeability method specific surface area of 0.1 m²/g and no DTA exothermic peak observable was mixed with a similar co-catalyst to form 3 parts of a catalyst mixture, which was used as the copper catalyst.

The results are shown in Table 1.

TABLE 1

| | EX 1 stamped | EX 2 stamped | EX 3 atomized powder | EX 4 stamped | CE 1 stamped and annealed | CE 2 electrolytic copper powder |
|---|---|---|---|---|---|---|
| Metallic copper catalyst | | | | | | |
| Co-catalyst | zinc-tin | zinc-tin | zinc-tin | zinc-tin-antimony | zinc-tin | zinc-tin |
| Air-permeability method specific surface area (m²/g) | 0.88 | 0.30 | 1.4 | 0.30 | 0.70 | 0.10 |
| DTA heat generation start temperature (° C.) | 218 | 230 | 159 | 230 | Nil | Nil |
| DTA calorific value (cal/g) | 24.9 | 7.6 | 52.7 | 7.6 | Nil | Nil |
| Average rate of silane production (g-silane/100 g-hr) | 18.5 | 15.3 | 21.5 | 16.3 | 10.2 | 2.5 |
| $CH_3(H)SiCl_2$ (%) | 1.8 | 2.3 | 1.5 | 2.1 | 6.5 | 10.3 |
| $(CH_3)_2SiCl_2$ (%) | 90 | 82 | 91 | 85 | 75 | 46 |
| $CH_3SiCl_3/(CH_3)_2SiCl_2$ ratio | 0.050 | 0.091 | 0.045 | 0.055 | 0.20 | 0.68 |

There has been described a thermally active copper catalyst having a large quantity of internal strain energy for use in the Rochow reaction of directly reacting an organic halide with metallic silicon powder to synthesize organohalosilanes. The inventive catalyst is effective for reducing the activation time taken until the reaction reaches a steady state, which has been the neck of the Rochow reaction, improving selectivity in the steady state, and increasing the yield from silicon. Although the prior art employs, because of the importance of the copper catalyst, the pretest procedure that the copper catalyst is subject to a separate test to evaluate its activity before it is used in an industrial plant, the invention eliminates the pretest procedure.

Japanese Patent Application No. 11-064335 is incorporated herein by reference.

Reasonable modifications and variations are possible from the foregoing disclosure without departing from either the spirit or scope of the present invention as defined by the claims.

What is claimed is:

1. A metallic copper catalyst, comprising a thermally active metallic copper powder having a heat generation start temperature of up to 300° C. and a calorific value of 1 to 80 cal/g upon differential thermal analysis in an air stream.

2. The copper catalyst of claim 1 wherein the metallic copper powder is a copper foil powder, stamped copper powder or microscopic copper powder.

3. The copper catalyst of claim 1 having a specific surface area of 0.05 to 2 m²/g as measured by the BET method or air-permeability method.

4. A process for preparing organohalosilanes by reacting an organic halide with metallic silicon particles in the presence of a metallic copper catalyst, said metallic copper catalyst being the copper catalyst of claim 1.

5. A metallic copper catalyst comprising a thermally active metallic copper powder having crystal lattices whose strain energy is relaxed at below 300° C.

6. The copper catalyst of claim 5 wherein the metallic copper powder is a copper foil powder, stamped copper powder or microscopic copper powder.

7. The copper catalyst of claim 5 having a specific surface area of 0.05 to 2 $m^2/g$ as measured by the BET method or air-permeability method.

8. A process for preparing organohalosilanes by reacting an organic halide with metallic silicon particles in the presence of a metallic copper catalyst, said metallic copper catalyst being the copper catalyst of claim 5.

* * * * *